(12) United States Patent
Schenck Mortell et al.

(10) Patent No.: US 8,292,868 B2
(45) Date of Patent: Oct. 23, 2012

(54) PROCESS TO MAKE BOXER SHORTS HAVING A CONTRACTED CROTCH REGION

(75) Inventors: Heather Schenck Mortell, Neenah, WI (US); Joseph Daniel Coenen, Neenah, WI (US); Robert Lee Popp, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 145 days.

(21) Appl. No.: 12/466,838

(22) Filed: May 15, 2009

(65) Prior Publication Data

US 2009/0217442 A1    Sep. 3, 2009

Related U.S. Application Data

(63) Continuation of application No. 10/314,915, filed on Dec. 9, 2002, now abandoned.

(51) Int. Cl.
 *A61F 13/15* (2006.01)
 *A41B 9/02* (2006.01)
 *A41B 9/04* (2006.01)
(52) U.S. Cl. ............... 604/396; 604/385.3; 604/385.03; 604/385.05; 604/385.14; 604/385.22; 604/385.23; 604/385.24; 2/401; 2/402; 2/404; 2/407
(58) Field of Classification Search ............... 604/385.22–385.29, 385.3, 396, 604/385.03, 385.05, 385.14; 2/401, 402, 2/404, 407
See application file for complete search history.

(56) References Cited

U.S. PATENT DOCUMENTS

| | | | |
|---|---|---|---|
| 478,281 | A | 7/1892 | Hamilton et al. |
| 1,577,409 | A | 3/1926 | Rand |
| 1,664,298 | A | 3/1928 | Katz |
| 1,971,558 | A | 8/1934 | Goodman |
| 2,030,306 | A | 2/1936 | Lain |
| 2,032,982 | A | 3/1936 | Gerstman |
| 2,088,302 | A | 7/1937 | McKeever |
| 2,116,822 | A | 5/1938 | Berger |
| 2,242,526 | A | 5/1941 | Kneibler |
| 2,252,019 | A | 8/1941 | Meinecke et al. |
| 2,319,138 | A | 5/1943 | Kneibler |
| 2,391,641 | A | 12/1945 | Mildred |
| 2,435,945 | A | 2/1948 | Redmond |
| 2,450,789 | A | 10/1948 | Frieman |
| 2,522,510 | A | 9/1950 | Fridolph |
| 2,538,596 | A | 1/1951 | Sheridan |
| 2,675,806 | A | 4/1954 | Bram |
| 2,711,735 | A | 6/1955 | Sabo |
| 2,838,047 | A | 6/1958 | Sidnell |
| 2,842,129 | A | 7/1958 | Ernstorff |

(Continued)

FOREIGN PATENT DOCUMENTS

CA    2356510    2/2003

(Continued)

*Primary Examiner* — Jacqueline F. Stephens
(74) *Attorney, Agent, or Firm* — Armstrong Teasdale LLP

(57) ABSTRACT

A pant has a garment shell. The garment shell includes a front region, a back region, a contracted crotch region, side seams connecting the front region to the back region, two leg openings, and hanging legs. At least a portion of each of the front region, the back region, the contracted crotch region and the hanging legs include portions of a single flat web. The hanging legs include no elasticization around a full periphery of the leg openings and are adapted to hang loosely about a wearer's thigh.

31 Claims, 12 Drawing Sheets

U.S. PATENT DOCUMENTS

| | | | |
|---|---|---|---|
| 2,859,752 A | 11/1958 | Haber | |
| 3,245,407 A | 4/1966 | Mason | |
| 3,338,992 A | 8/1967 | Kinney | |
| 3,341,394 A | 9/1967 | Kinney | |
| 3,386,442 A | 6/1968 | Sabee | |
| 3,418,660 A | 12/1968 | Shumate | |
| 3,502,538 A | 3/1970 | Petersen | |
| 3,502,763 A | 3/1970 | Hartman | |
| 3,542,615 A | 11/1970 | Dobo et al. | |
| 3,692,618 A | 9/1972 | Dorschner et al. | |
| 3,739,398 A | 6/1973 | Sarmiento | |
| 3,802,817 A | 4/1974 | Matsuki et al. | |
| 4,106,125 A | 8/1978 | Palumbo | |
| 4,284,454 A | 8/1981 | Joa | |
| 4,310,929 A | 1/1982 | Finlay | |
| 4,327,448 A | 5/1982 | Lunt | |
| 4,340,563 A | 7/1982 | Appel et al. | |
| 4,397,704 A | 8/1983 | Frick | |
| 4,417,938 A | 11/1983 | Sigl | |
| 4,543,141 A | 9/1985 | Bradley et al. | |
| 4,555,245 A * | 11/1985 | Armbruster | 604/396 |
| 4,608,115 A | 8/1986 | Schroth et al. | |
| 4,646,362 A | 3/1987 | Heran et al. | |
| 4,650,530 A | 3/1987 | Mahoney et al. | |
| 4,663,106 A | 5/1987 | Pomplun et al. | |
| 4,665,306 A | 5/1987 | Roland et al. | |
| 4,704,116 A | 11/1987 | Enloe | |
| 4,771,483 A | 9/1988 | Hooreman et al. | |
| 4,816,094 A | 3/1989 | Pomplun et al. | |
| 4,850,992 A | 7/1989 | Amaral et al. | |
| 4,892,536 A | 1/1990 | DesMarais et al. | |
| 4,895,568 A | 1/1990 | Enloe | |
| 4,935,021 A | 6/1990 | Huffman et al. | |
| D315,050 S | 3/1991 | Bush et al. | |
| 5,046,272 A | 9/1991 | Vogt et al. | |
| 5,147,487 A | 9/1992 | Nomura et al. | |
| 5,171,388 A | 12/1992 | Hoffman et al. | |
| 5,187,817 A | 2/1993 | Zolner | |
| 5,382,246 A | 1/1995 | Kawano | |
| 5,554,149 A | 9/1996 | O'Donnell | |
| 5,556,504 A | 9/1996 | Rajala et al. | |
| 5,704,071 A | 1/1998 | Barclay et al. | |
| 5,716,478 A | 2/1998 | Boothe et al. | |
| 5,733,401 A | 3/1998 | Linman et al. | |
| 5,755,902 A | 5/1998 | Reynolds | |
| 5,759,340 A | 6/1998 | Boothe et al. | |
| 5,921,974 A | 7/1999 | Kikuchi | |
| 5,956,774 A | 9/1999 | Mackley | |
| 6,022,443 A | 2/2000 | Rajala et al. | |
| 6,168,585 B1 | 1/2001 | Cesco-Cancian | |
| 6,205,592 B1 | 3/2001 | Gouws | |
| 6,248,097 B1 | 6/2001 | Beitz | |
| 6,287,169 B1 | 9/2001 | Willms et al. | |
| 6,319,347 B1 | 11/2001 | Rajala et al. | |
| 6,610,901 B2 | 8/2003 | McMahon-Ayerst et al. | |
| 6,626,883 B2 | 9/2003 | Wada et al. | |
| 6,666,851 B2 | 12/2003 | Otsubo et al. | |
| 6,807,685 B1 | 10/2004 | Hasegawa et al. | |
| 2001/0014798 A1 | 8/2001 | Fernfors | |
| 2002/0000291 A1 | 1/2002 | Coenen et al. | |
| 2002/0099345 A1 | 7/2002 | Saito et al. | |
| 2003/0109842 A1 | 6/2003 | Louis et al. | |
| 2003/0115660 A1 | 6/2003 | Hopkins | |
| 2004/0098791 A1 | 5/2004 | Faulks | |
| 2004/0102746 A1 | 5/2004 | Mortell et al. | |
| 2004/0107481 A1 | 6/2004 | Mortell et al. | |
| 2004/0116881 A1 | 6/2004 | Nordness et al. | |

FOREIGN PATENT DOCUMENTS

| | | |
|---|---|---|
| EP | 0717971 | 6/1996 |
| GB | 620555 | 3/1949 |
| GB | 2069820 | 9/1981 |
| GB | 2112268 | 7/1983 |
| JP | 4-242643 | 8/1992 |
| JP | 2000-93462 | 4/2000 |
| JP | 2002095700 | 4/2002 |
| JP | 2004159949 | 6/2004 |
| WO | 9925299 A1 | 5/1999 |
| WO | 01/03524 | 1/2001 |
| WO | 01/87217 | 11/2001 |
| WO | 01/87218 | 11/2001 |
| WO | 01/87562 | 11/2001 |
| WO | 01/87753 | 11/2001 |
| WO | 02/49565 | 6/2002 |
| WO | 02/052967 | 7/2002 |
| WO | 03/041625 A1 | 5/2003 |
| WO | 03/057107 A1 | 7/2003 |
| WO | 2004052131 A1 | 6/2004 |
| WO | 2004/062398 | 7/2004 |
| WO | 2004/073430 A2 | 9/2004 |

* cited by examiner

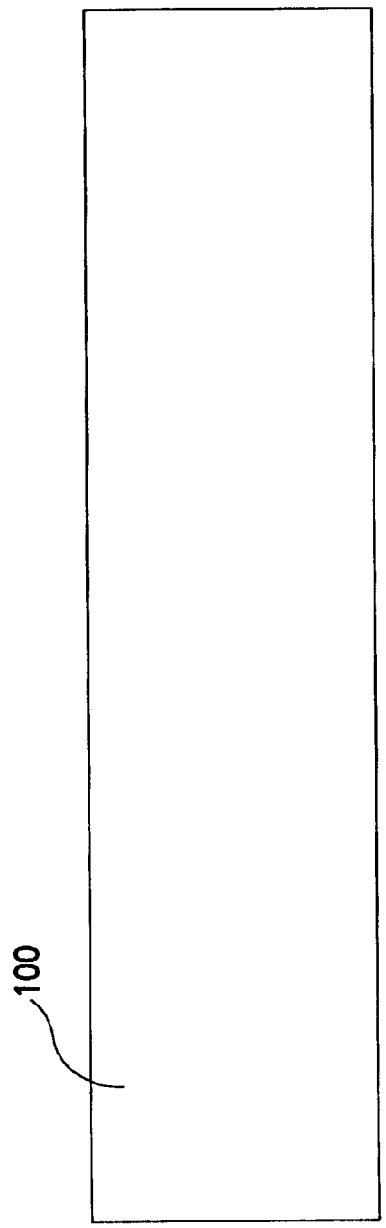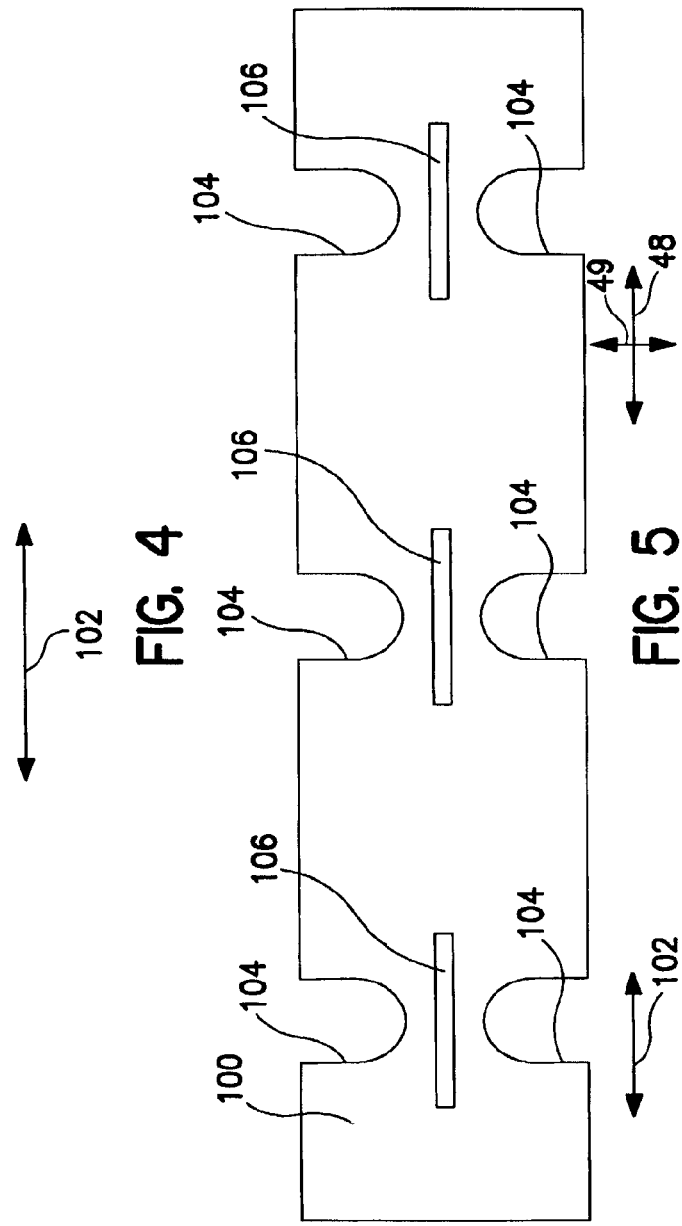

PROCESS TO MAKE BOXER SHORTS HAVING A CONTRACTED CROTCH REGION

CROSS REFERENCE TO RELATED APPLICATION

This application is a continuation of U.S. patent application Ser. No. 10/314,915, filed on Dec. 9, 2002, which is hereby incorporated by reference in its entirety.

BACKGROUND OF THE INVENTION

The present invention pertains to methods of making pants having side seams and a contracted crotch region. More particularly, the present invention pertains to methods of making boxer shorts having side seams and a contracted crotch region. The boxer shorts may be absorbent or non-absorbent.

Pant-like garments have numerous applications including disposable clothing, training pants, feminine care products, adult incontinence products, disposable swimwear, or the like. Pant-like disposable garments are typically three-dimensional products with closed sides so that the product has a unitary waist opening and two leg openings. The wearer raises and lowers the garment to apply the product. Three-dimensional, boxer shorts-like products are particularly appealing because the boxer shorts look more like conventional articles of clothes.

Many disposable pants are formed as composite structures in which several components are combined to form a product specifically suited to its intended purpose. For example, disposable pants often include one or more absorbent materials intended to absorb various bodily exudates such as urine, menstrual fluid, and/or sweat. Such products may include a liquid permeable bodyside liner and a liquid impermeable outer cover, and can include other materials and features such as elastic materials and containment structures.

However, many disposable pants are aesthetically unappealing. Existing disposable absorbent pants can be overly bulky and often resemble disposable baby diapers. Various attempts have been made to provide disposable pants having an improved, more clothing-like appearance. However, disposable pants, particularly disposable absorbent boxer shorts, present many manufacturing challenges. In part, this is due to the high speed that is necessary to economically produce relatively low-cost disposable absorbent products. Product design is often compromised by cost and manufacturing constraints, resulting in disposable pants that lack aesthetic appeal and product function. In addition, crotch depth is required for a good fit, but difficult to achieve in a garment like boxer-shorts with hanging legs when using conventional manufacturing processes.

Thus, what is lacking and needed in the art are garment-like, aesthetically appealing boxer shorts, as well as methods of efficiently manufacturing such boxer shorts.

BRIEF DESCRIPTION OF THE INVENTION

In one aspect, a pant includes a garment shell made from a single flat web. The pant generally comprises a garment shell. The garment shell includes a front region, a back region, a contracted crotch region, side seams connecting the front region to the back region, two leg openings, and hanging legs. At least a portion of each of the front region, the back region, the contracted crotch region and the hanging legs comprise portions of the single flat web. The hanging legs include no elasticization around a full periphery of the leg openings and are adapted to hang loosely about a wearer's thigh.

In another aspect, a pant includes a garment shell made from a web. The pant generally comprises a garment shell. The garment shell includes a front region, a back region, a contracted crotch region, a front waist edge, a back waist edge, side seams connecting the front region to the back region, two leg openings, and hanging legs. At least a portion of each of the front region, the back region, the contracted crotch region and the hanging legs comprise portions of the web. The hanging legs are adapted to hang loosely about a wearer's thigh. An absorbent structure is attached to the garment shell in at least one of the front region, the back region, and the crotch region. The contracted crotch region is positioned approximately midway between the side seams.

In yet another aspect, a pant includes a garment shell made from a web. The pant generally comprises a garment shell. The garment shell includes a front region, a back region, a contracted crotch region, a front waist edge, a back waist edge, side seams connecting the front region to the back region, two leg openings and hanging legs. At least a portion of each of the front region, the back region, the contracted crotch region and the hanging legs comprise portions of the web. The contracted crotch region is positioned approximately midway between the two leg openings. The hanging legs include no elasticization around a full periphery of the leg openings and are adapted to hang loosely about a wearer's thigh.

In a further aspect, a pant includes a garment shell made from a web. The pant generally comprises a garment shell. The garment shell includes a front region, a back region, a contracted crotch region, a front waist edge, a back waist edge, two leg openings and hanging legs. A strip in the contracted crotch region is positioned approximately midway between the two leg openings. At least a portion of each of the front region, the back region, the contracted crotch region and the hanging legs comprise portions of the web. The strip is straight, defines a length, and extends in a direction substantially perpendicular to each waist edge along its entire length. The hanging legs include no elasticization around a full periphery of the leg openings and are adapted to hang loosely about a wearer's thigh.

In still yet another aspect, a pant includes a garment shell made from a web. The pant generally comprises a garment shell. The garment shell includes a front region, a back region, a contracted crotch region, a front waist edge, a back waist edge, side seams connecting the front region to the back region, two leg openings and hanging legs. An absorbent structure is attached to the garment shell in at least one of the front region, the back region, and the crotch region. At least a portion of each of the front region, the back region, the contracted crotch region and the hanging legs comprise portions of the web. The contracted crotch region is positioned approximately midway between the two leg openings with an elastomeric strip positioned in the contracted crotch region approximately midway between the two leg openings. The elastomeric strip is straight, defines a length, and extends in a direction substantially perpendicular to each waist edge along its entire length. The hanging legs include no elasticization around a full periphery of the leg openings and are adapted to hang loosely about a wearer's thigh.

BRIEF DESCRIPTION OF THE DRAWINGS

FIG. 4 is a top view of a flat web;

FIG. 5 is a top view of the flat web of FIG. 4 including leg openings and strips applied to the flat web for assembling pants according to one embodiment of the invention in the machine direction;

DEFINITIONS

Figure 1:
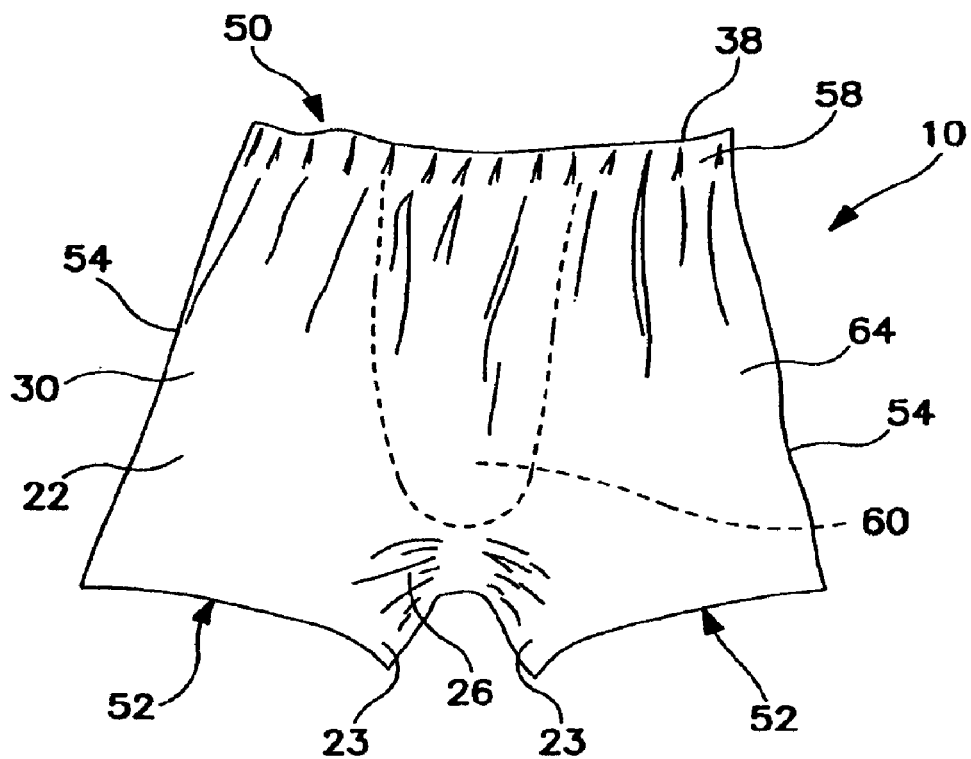
FIG. 1 is a front view of one embodiment of a pant according to the present invention.

Within the context of this specification, each term or phrase below will include the following meaning or meanings.

"Attached" refers to the joining, adhering, connecting, bonding, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Boxer shorts" refers to a garment having hanging legs.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Corrugated" refers to the condition of a material which has been gathered into pleats or regular rugosites or folds, the material being shortened thereby.

"Disposable" refers to articles which are designed to be discarded after a limited use rather than being laundered or otherwise restored for reuse.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all woven, knitted and non-woven fibrous webs.

"Flat web" comprises any material used for making garments that can be provided and processed in a substantially open, unfolded state; while the web can possess ripples or areas that do not lie exactly within an overall plane of the web, all points of the web should be reasonably identifiable as constituents in either an upper or a lower surface of the web. No portions of a flat web are enclosed or fixed into a loop or tunnel-like, or three-dimensional configuration.

"Garment shell" refers to an outer cover or outer layer of a garment. In a single-ply garment, the single layer of the garment is the garment shell.

"Garment insert" refers to an inner layer of a garment. The garment insert provides a close-to-the-body fit about a wearer's lower torso, thereby serving as a form of built-in underwear within the garment.

"Hanging legs" refers to the portions of a garment which extend from the crotch region downward to the leg openings. "Downward" refers to a direction toward the ground when the garment is positioned on a standing wearer.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

"Integral" is used to refer to various portions of a single unitary element rather than separate structures bonded to or placed with or placed near one another.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Machine direction" refers to the length of a fabric in the direction in which it is produced, as opposed to "cross-machine direction" which refers to the width of a fabric in a direction generally perpendicular to the machine direction.

The term "machine direction assembly" refers to a manufacturing process in which disposable products travel in an end-to-end or waist-to-waist orientation, in the longitudinal direction shown by arrow 48 in FIG. 5. A process utilizing a machine direction assembly entails products traveling through a converting machine parallel to the direction of arrow 102, as opposed to "cross-machine direction assembly" in which the products travel in a side-by-side orientation such as that shown by arrow 49 in FIG. 10.

"Member" when used in the singular can have the dual meaning of a single element or a plurality of elements.

"Nonwoven" and "nonwoven web" and "web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542, 615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns.

"Stretchable" means that a material can be stretched, without breaking, by at least 50% (to 150% of its initial (unstretched) length) in at least one direction, suitably by at least 100% (to 200% of its initial length), desirably by at least 150% (to at least 250% of its initial length).

"Surface" includes any layer, film, woven, nonwoven, laminate, composite, or the like, whether pervious or impervious to air, gas, and/or liquids.

"Three-dimensional garment" refers to a garment that cannot be laid flat with all of its seams in one plane.

These terms may be defined with additional language in the remaining portions of the specification.

DETAILED DESCRIPTION OF THE DRAWINGS

Figure 2A:
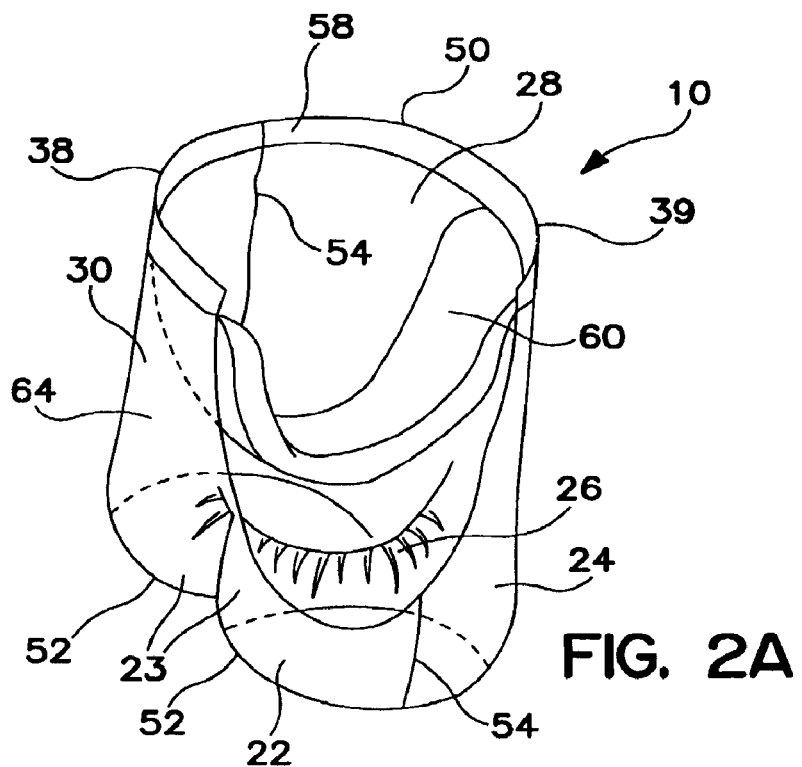
FIG. 2A is a perspective cut-away view of one embodiment of a pant according to the present invention.
Figure 2B:
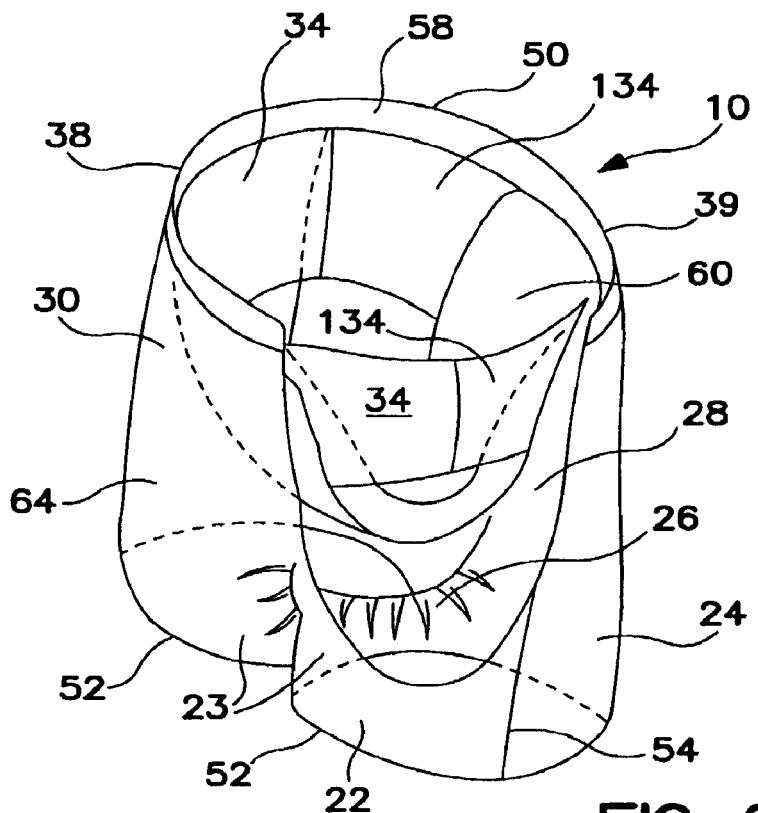
FIG. 2B is a perspective cut-away view of one embodiment of a pant according to the present invention.

As representatively illustrated in FIGS. 1, 2A and 2B, an embodiment of a pant 10 of the present invention includes a garment shell 64. The garment shell 64 can include a front region 22, a back region 24, a contracted crotch region 26, an inner surface 28 which is configured to contact the wearer, and an outer surface 30 opposite the inner surface 28 which is configured to contact the wearer's clothing. The pant 10 also defines a pair of longitudinally opposed waist edges, which are designated front waist edge 38 and back waist edge 39. The front region 22 is contiguous with the front waist edge 38, and the back region 24 is contiguous with the back waist edge 39. The front region 22 includes the portion of the pant 10 which, when worn, is positioned on the front of the wearer while the back region 24 includes the portion of the pant 10 which, when worn, is positioned on the back of the wearer. The contracted crotch region 26 of the pant 10 includes the portion of the pant which, when worn, is positioned between the legs of the wearer and covers the lower torso of the wearer. As illustrated in FIGS. 1, 2A and 2B the front and back regions 22 and 24 are joined together at side seams 54 to define a three-dimensional pant configuration having a waist opening 50 and a pair of leg openings 52. In particular embodiments, the pant 10 can include an absorbent structure 60. Various embodiments of these and other features will now be described.

The garment shell 64 includes a contracted crotch region 26. As described more fully below, the contraction of the contracted crotch region 26 can be accomplished either elastically or inelastically. The contracted crotch region 26 provides crotch depth that provides a good fit through the contracted crotch region 26. The garment shell 64 can also include hanging legs 23 which extend from the contracted crotch region 26 downward to the leg openings 52 (FIGS. 1, 2A and 2B).

The pant 10 also includes side seams 54 which connect the front region 22 to the back region 24 to create the pant 10. The side seams 54 can take any number of forms, including both refastenable and non-refastenable seams as is known in the art. The provision of the side seams 54 can be accomplished in the manner described in U.S. Pat. No. 5,046,272, issued Sep. 10, 1991 to Vogt et al., which is incorporated herein by reference, or in the manner described in PCT Publications WO 01/87562 by Tomsovic, et al., WO 01/87217 by Durrance, et al., WO 01/87753 by Hietpas, and or WO 01/87218 by Vogt, et al., all of which are incorporated herein by reference. As is known in the art, the side seams 54 can be inward or outward fin seams or lap seams (not shown).

The pant 10 can also have a waist elastic member 58 extending along at least a portion of the front waist edge 38 and/or the back waist edge 39. The waist elastic member 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the waist elastic member 58 includes a plurality of dry-spun coalesced multifilament spandex elastomeric threads sold under the trade name LYCRA® and available from E.I. du Pont de Nemours and Company, Wilmington, Del., U.S.A. Alternatively, multiple strands of 310 decitex LYCRA® may be also laminated at 250% elongation between spunbond facings in addition to an adhesive.

As another alternative, the waist elastic member 58 can be a material exhibiting delayed retraction, or can in fact be non-elastic. Delayed retraction materials may include those designed to retract relatively slowly following compression, such as "temporarily inhibited" elastic materials. "Temporarily inhibited" materials are described, for example, in U.S. Pat. No. 5,545,158 issued Aug. 13, 1996, to Jessup, U.S. Pat. No. 5,669,996 issued Sep. 23, 1997, to Jessup, and U.S. Pat. No. 5,500,063 issued Mar. 19, 1996, to Jessup, all of which are herein incorporated by reference, and references cited therein. Alternatively, a delayed retraction material may be designed to resist retraction until an activation process occurs, such as so-called "latent elastic" materials. Suitable retractive materials for use as a delayed retraction material can alternatively comprise any material adapted to retract upon activation, whether immediately upon activation or subsequently thereto. The retractive material can comprise elastomeric or nonelastomeric materials. Suitable nonelastomeric retractive materials can comprise without limitation polyether block amides (PEBAX®) or the like, and laminates thereof. Suitable elastromeric retractive materials can comprise without limitation LYCRA® materials, elastomeric materials including latex or rubber or synthetic urethanes, or the like, and laminates thereof. In particular embodiments, the retractive material can comprise an elastomeric material having an unstable state relative to some other stable and elastic state. In such embodiments, the retractive material can, but need not, have elastomeric properties in the unstable state. Other examples include heat-shrinkable elastic materials such as described in U.S. Pat. No. 4,816,094 issued Mar. 28, 1989 to Pomplun et al., U.S. Pat. No. 4,665,306 issued May 12, 1987 to Roland et al., and U.S. Pat. No. 4,663,106 issued May 5, 1987 to Pomplun et al., all of which are herein incorporated by reference.

A pant of this type can be designed to fit wearers in a wide range of sizes, by adjusting the pant dimensions based on the anthropometric features of an intended wearer. Ratios of wearer dimensions to pant dimensions for a suitable boxer-style pant have been determined and are shown in Table 1. In addition, stylistic variations such as hip-hugging (low rise), relatively more closely or loosely fitted shorts, and other styles, may be provided by varying the ratios listed in Table 1 within (or even beyond) the ranges shown. Moreover, the use of elastomeric or extensible material to form the garment shell may provide additional adaptability to fit a wider range of wearer sizes.

Figure 1A:
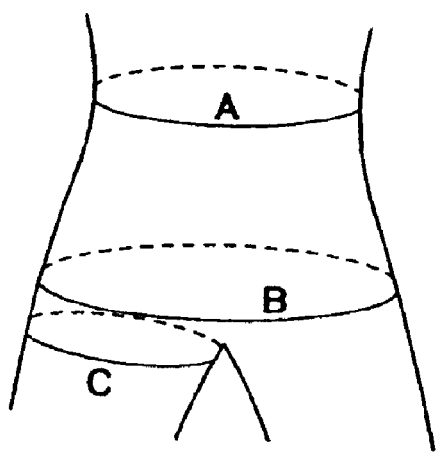
FIGS. 1A and 1B illustrate dimensions described with respect to Tables 1 and 2.
Figure 1B:
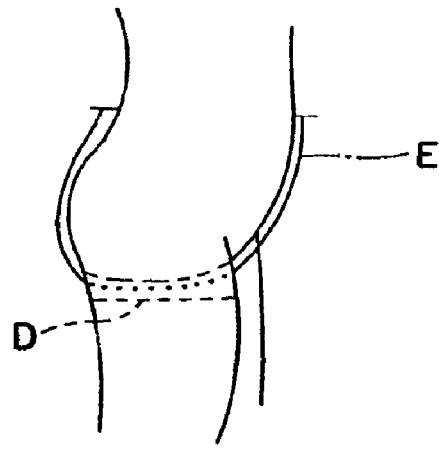
Figures 5A, 5B:
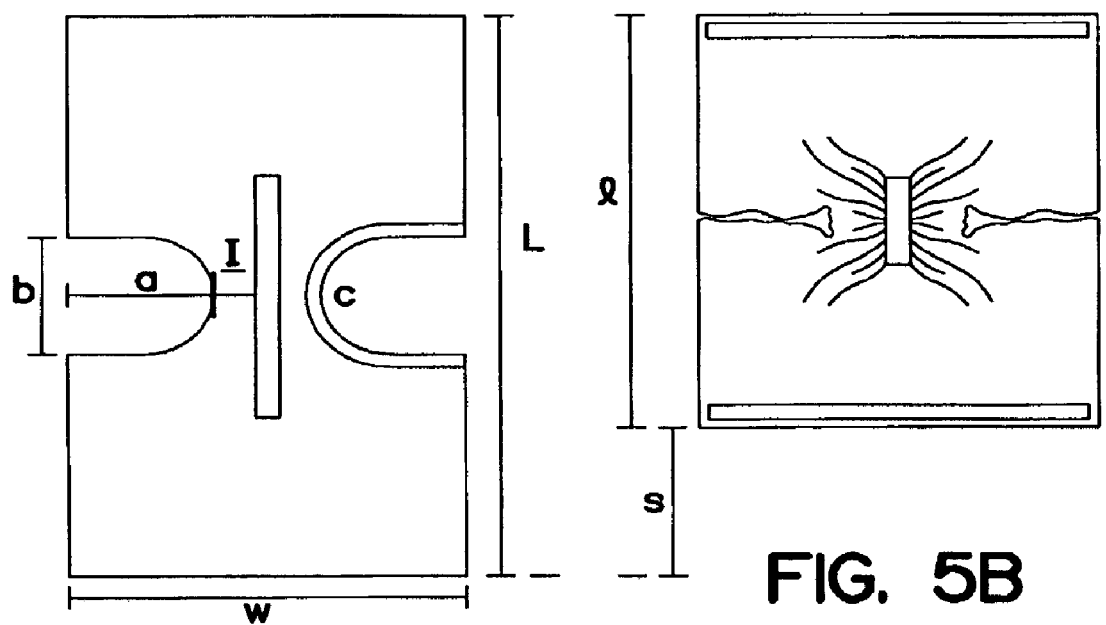
FIGS. 5A and 5B illustrate dimensions described with respect to Tables 1 and 2.

Since the pant dimensions are determined by the dimensions of the intended wearer, the ratios shown are based upon five measurements of an intended wearer, abbreviated as follows:

A: waist circumference (FIG. 1A)
B: hip circumference (FIG. 1A)
C: thigh circumference (measured in crotch region, horizontally; see FIG. 1A)
D: crotch depth (measured in crotch region, viewed 18 inches from the wearer's side; see FIG. 1B)
E: center front waist to center back waist through crotch; see FIG. 1B Table 2 shows how garment shell dimensions shown in FIGS. 5A and 5B are determined using body measurements A-E and ratios in Table 1. Table 2 also shows how the ratios in Table 1 have been applied to create shorts for two different size wearers, one a mannequin of a child (Wearer #1) weighing approximately 32 to 40 pounds (15-18 Kg), the other an adult female (Wearer #2) weighing approximately 125 pounds (57 Kg).

TABLE 1

| PANT DIMENSIONS | DETAILS and RATIOS | EXEMPLARY RANGES |
| --- | --- | --- |
| Garment inseam I (FIG. 5A, dimension "I") | Selected based on garment style. There is not a seam at this location; this is simply the location where an "inseam" measurement is generally taken. After contraction, this dimension "I" provides the "hanging legs" feature of the pant. | 1-5 inches, or more |
| Width of garment shell (FIG. 5A, dimension "w") | Ratio of 2x Width (i.e., garment circumference) to the larger of wearer's Hip or Waist circumference 2w:[B or A] | From about 1.2:1 to about 2:1, such as about 1.7, e.g., 2w = 1.2A or 1.2B |
| Length of base of arc (FIG. 5A, dimension "b") | Ratio of Arc base length to Wearer crotch depth b:D | From about 1:1 to about 1.5:1, such as about 1.25:1 |
| Circumference of leg opening (FIG. 5A, dimension "c") | Ratio of Leg opening to Wearer thigh circumference c:C | From about 1.1:1 to about 1.5:1, such as about 1.25:1 |
| Takeup (shortening) of garment shell on gathering of crotch (FIG. 5B, dimension "s") | Ratio of Takeup to 2x Garment inseam length I s:2I | From about 1:1 to about 1.6:1, such as about 1.3:1 |
| Length of garment shell after gathering (FIG. 5B, dimension "l") | Ratio of Length after gathering to Wearer F to B waist thru crotch 1:E | This can vary widely depending on the desired short style, but for a standard fit, from about 1.1:1 to about 1.4:1, such as about 1.25:1, e.g. 1 = 1.4E |
| Length of garment shell before gathering (FIG. 5A, dimension "L") Arc height (FIG. 5A, dimension "a") | Sum of Takeup and Length of shell after gathering s + 1 (Width of garment shell − 2x Garment inseam I)/2 (w − 2I)/2 | |

TABLE 2

| | Wearer #1 | Short #1 | Wearer #2 | Short #2 |
| --- | --- | --- | --- | --- |
| A | 50 cm | | 78 cm | |
| B | 54 cm | | 96 cm | |
| C | 29 cm | | 55 cm | |
| D | 10 cm | | 16.5 cm | |
| E | 41 cm | | 61 cm | |
| I | | 6 cm | | 8 cm |
| w | | 45 cm | | 67 cm |
| b | | 12.5 cm | | 20.5 cm |
| c | | 36 cm | | 68 cm |
| s | | 15.5 cm | | 21 cm |
| l | | 50.5 cm | | 75 cm |
| L | | 66 cm | | 96 cm |
| a | | 15 cm | | 25 cm |

The pant 10 can also include an absorbent structure 60. The absorbent structure 60 can be attached to the garment shell 64 at the front waist edge 38 and back waist edge 39, or at some point below the front waist edge 38 and back waist edge 39 on the front region 22 and back region 24. (FIGS. 2A and 2B). Alternatively, the absorbent structure 60 can be attached to the garment shell 64 in the contracted crotch region 26.

The absorbent structure 60 can be any structure which is generally compressible, conformable, non-irritating to the skin, and capable of absorbing and retaining liquids and certain body wastes. The absorbent structure 60 can be manufactured in a wide variety of sizes and shapes, from a wide variety of liquid absorbent materials commonly used in the art, and may be stretchable, non-stretchable, or elastic. For example, the absorbent structure 60 can suitably include a matrix of hydrophilic fibers, such as a web of cellulosic fluff, mixed with particles of a high-absorbency material commonly known as superabsorbent material. In a particular embodiment, the absorbent structure 60 includes a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent structure 60 to better contain and absorb body exudates. The concentration of the superabsorbent particles can also vary through the thickness of the absorbent structure 60. Alternatively, the absorbent structure 60 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent structure 60 includes a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent structure 60 in an amount of from 0 to about 90 weight percent based on total weight of the absorbent assembly. The absorbent structure 60 suitably has a density within the range of about 0.10 to about 0.35 grams per cubic centimeter. The absorbent structure 60 may or may not be wrapped or encompassed by a suitable tissue wrap that may help maintain the integrity and/or shape of the absorbent assembly.

The absorbent structure 60 can also incorporate other materials that are designed primarily to receive, temporarily store, and/or transport liquid along the mutually facing surface with absorbent structure 60, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C. U.S.A.

In particular embodiments, the absorbent structure 60 is thin to provide a slim, comfortable, non-bulky pant 10. Any suitable thin absorbent structure may be used, such as for example, the thin absorbent described in WO 02/49565, published Jun. 27, 2002, by Sawyer et al., which is incorporated herein by reference.

The absorbent structure 60 can include a pair of containment flaps 62 (FIG. 3A) which are configured to provide a barrier to the transverse flow of body exudates. A flap elastic member (not shown) can be operatively joined with each containment flap 62 in any suitable manner as is well known in the art. The elasticized containment flaps 62 define an unattached edge which assumes an upright, generally perpendicular configuration to form a seal against the wearer's body. Suitable constructions and arrangements for the containment flaps 62 are generally well known to those skilled in the art and are described in U.S. Pat. No. 4,704,116 issued Nov. 3, 1987 to Enloe, which is incorporated herein by reference.

In the alternative, a pant-like garment insert could be used for the absorbent structure 60. For example, the pant-like garment insert suitably includes a body side liner, an outer cover, and an absorbent assembly between the body side liner and the outer cover, and side panels. Examples of suitable pant-like garment inserts include a training pant, such as HUGGIES® PULL-UPS® Disposable Training Pants, or a disposable underpant, such as GOODNIGHTS® Disposable Underpants, both manufactured by Kimberly-Clark Corporation, Neenah, Wis., U.S.A. A training pant as the pant-like garment insert for the absorbent structure 60 can include front side panels 34 and back side panels 134 (FIGS. 2B and 3B). The manufacture of training pants having side panels can be accomplished in the manner described in U.S. patent application Ser. No. 09/855,484, filed May 15, 2001 (U.S. Publication U.S. 2002/0000291, Jan. 3, 2002) by Joseph D. Coenen et al., which is incorporated herein by reference.

As another alternative, a pad-type absorbent could be used for the absorbent structure. The pad-type absorbent can be attached in the crotch-region 26 of the pant 10. An example of a suitable pad-type absorbent is a feminine care pad such as KOTEX® Feminine Napkins, KOTEX® LIGHTDAYS® disposable panty liners, or an incontinence absorbent pad such as POISE® Feminine Guards and Pads or DEPEND® Guards for MEN, all manufactured by Kimberly-Clark Corporation, Neenah, Wis., U.S.A.

Figure 3A:
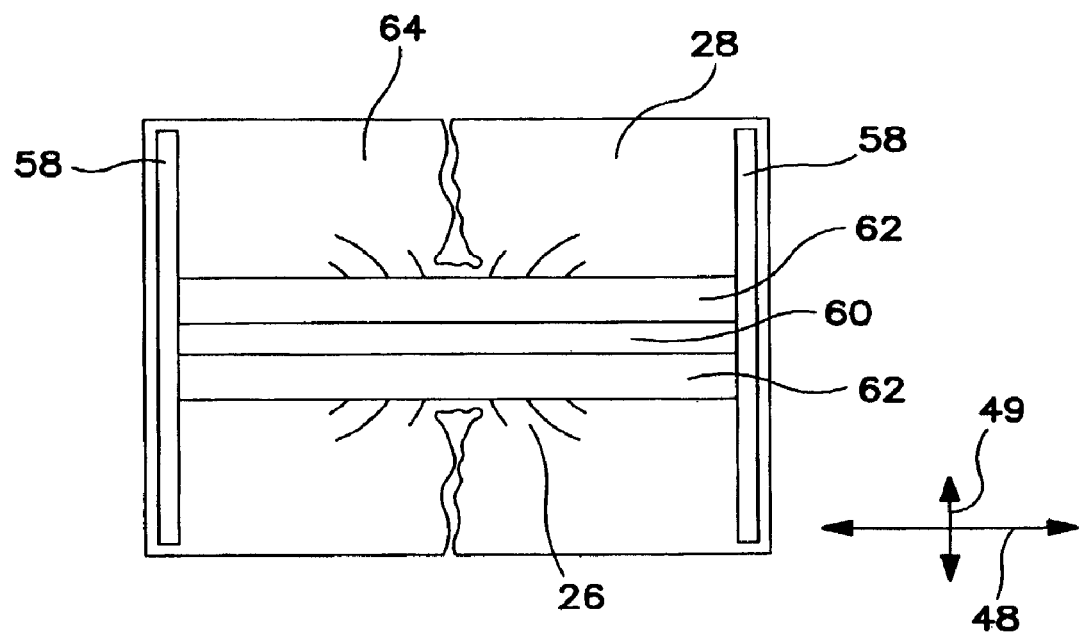
FIG. 3A is a plan view of the garment shown in FIG. 2A, showing the side facing the wearer.
Figure 3B:
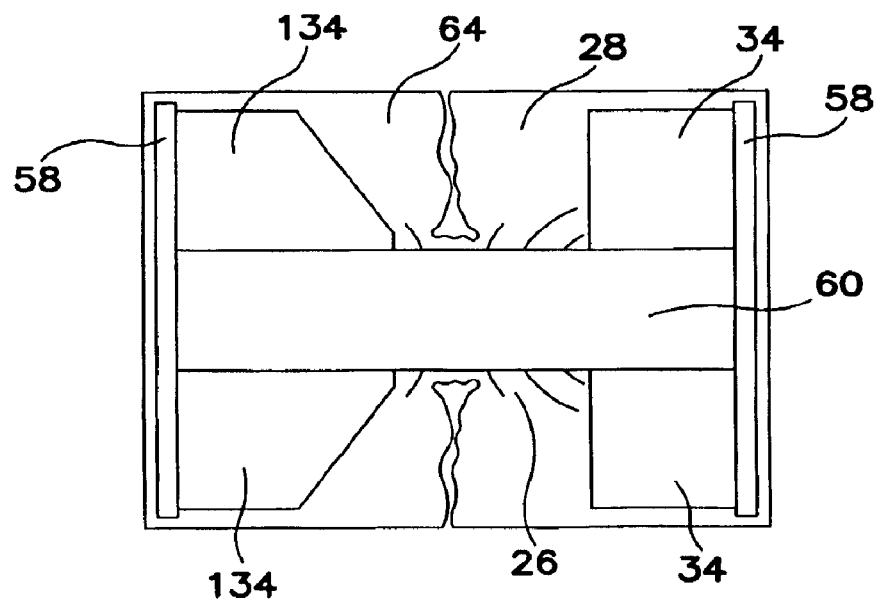
FIG. 3B is a plan view of the garment shown in FIG. 2B, showing the side facing the wearer.
Figure 3C:
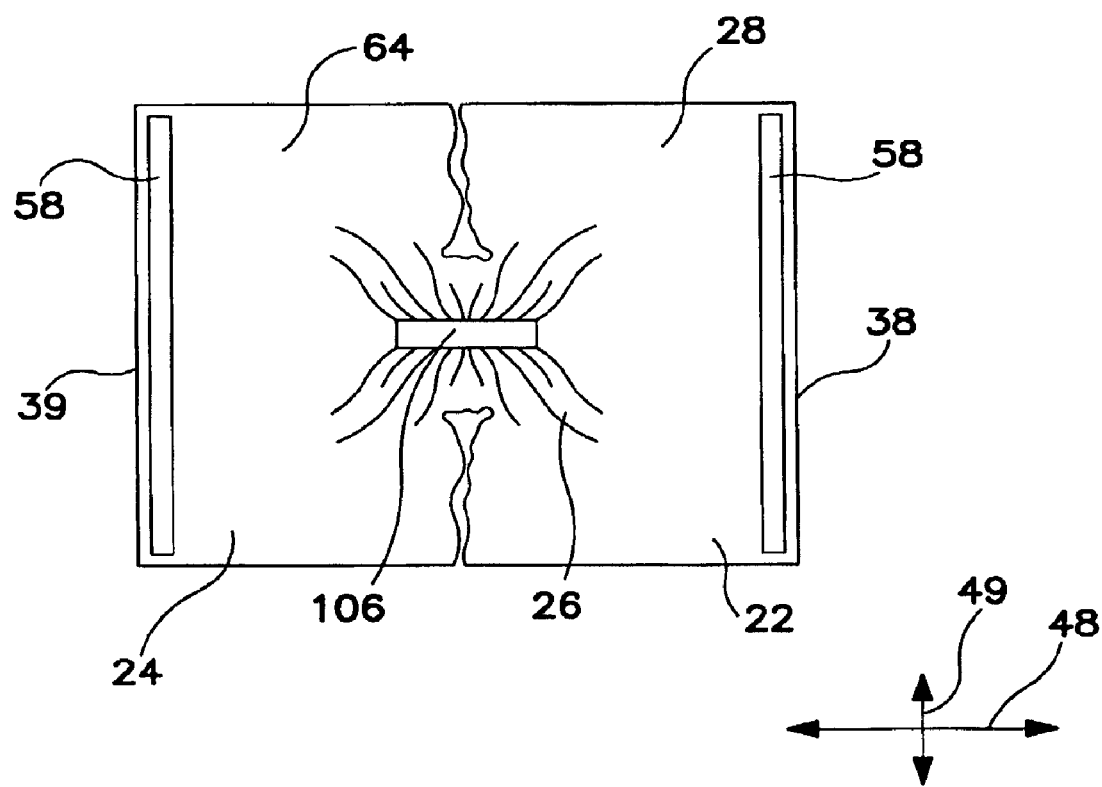
FIG. 3C is a plan view of the garment shown in FIG. 2A, showing the side facing the wearer without an absorbent structure.

For reference, arrows 48 and 49 depicting the orientation of the longitudinal axis and the transverse axis, respectively, of the garment shell 64 are illustrated in FIGS. 3A and 3C.

The garment shell 64 is desirably constructed of materials which are comfortable against the skin and non-irritating. It is contemplated that the garment shell 64 can be either disposable or durable, in the embodiments without an absorbent structure, and disposable in the embodiments with an absorbent structure. Both nonwoven and woven materials are contemplated for the garment shell 64. For example, the garment shell 64 for pant 10 can be selected from a wide variety of materials, including elastic, stretchable, or nonstretchable materials. The garment shell 64 can be a single layer of material or a multi-layered laminate structure. One example of a suitable material is a spunbond polypropylene nonwoven web. The garment shell 64 may also be made of those materials of which the absorbent structure 60 is made. It is desired that the garment shell 64 provides a relatively cloth-like texture to the wearer.

The present invention also includes various methods for making pants having side seams from a flat web, as shall now be explained and illustrated. Referring to FIG. 4, a single flat web 100 is provided moving in the direction represented by arrow 102. In the alternative, two webs that are joined at their edges to form a double-width piece (not shown) can be used for the flat web 100. The flat web 100 can be composed of any material previously described for the garment shell 64.

The method of the present invention can be carried out using machine direction assembly so that arrow 102 can correspond to the longitudinal direction as shown by arrow 48 (FIG. 5) with the products connected end to end or waist to waist, or the method of the present invention can be carried out using cross-machine direction assembly so that arrow 102 can correspond to the transverse direction as shown by arrow 49 (FIG. 10) with the products connected side-to-side.

In the machine direction process (FIGS. 5-9), portions of the flat web 100 are removed to define leg openings 104 (FIG. 5) by die cutting, or by any other suitable method known in the art. The leg openings 104, as more fully described below, become the leg openings 52 of the pant 10.

Strips 106 are applied to the selected areas located between the leg openings 104. Strips 106 can include elastic or non-elastic material. Examples of suitable non-elastic material include heat contractible materials, such as heat shrinkable films, for example, films formed of polyether block amides (PEBAX®, available from the Atofina Company of France) or the like. If the strips 106 are elastic, the elastic can be formed of any suitable material previously described for the waist elastic member 58. As an alternative, strips 106 can include any of the previously described delayed retraction materials.

Figure 7:
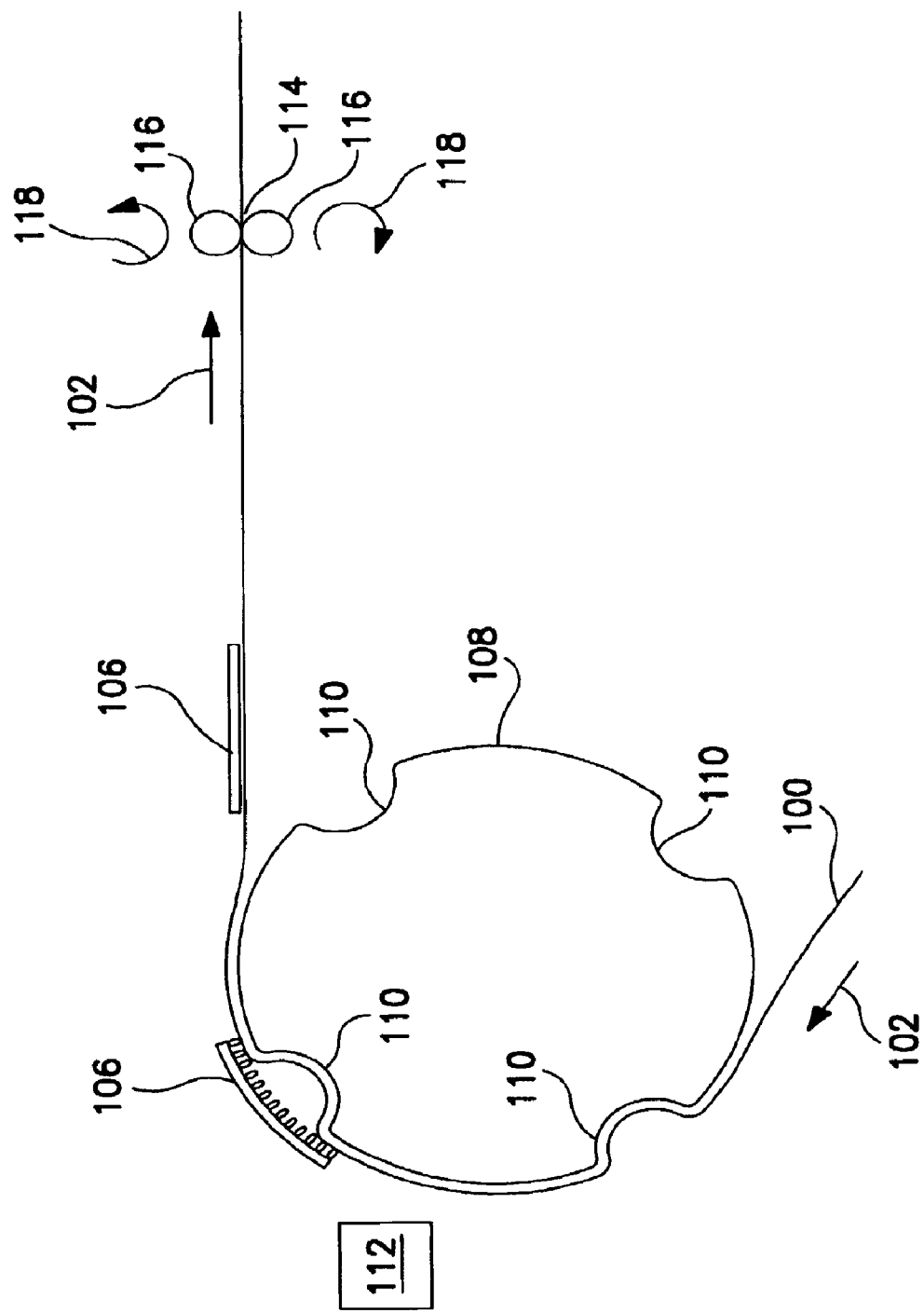
FIG. 7 is a side view of a looper drum for applying an elastic strip to the flat web.

Referring to FIG. 7, if the strips 106 are elastic, the strips 106 can be applied to the flat web 100 using a looper drum 108. Looper drums like looper drum 108 are known and are described, for example, in U.S. Pat. No. 5,171,388 issued Dec. 15, 1992 to Hoffman et al., herein incorporated by reference. Drum 108 includes surface grooves 110. Drum 108, as illustrated in FIG. 7, includes four surface grooves 110, but any number of surface grooves 110 may be included. The surface grooves 110 are spaced around the drum 108 so that each garment shell 64 eventually includes one strip 106. The flat web 100 travels around the drum 108 in the direction of arrow 102. The flat web 100 runs down into the surface grooves 110 by virtue of the fact that the drum 108 includes apertures across its surface and is under vacuum. Adhesive (shown for purposes of illustration as dots between strip 106 and the flat web 100 over the surface groove 110) is applied to the strip 106. In the alternative, the adhesive can be applied to the flat web 100 in the selected areas between leg openings 104. Suitable adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A The flat web 100 passes by the elastic application module 112 and the strip 106 of elastic is applied in a substantially unstretched condition to the flat web 100 over the surface groove 110. The flat web 100 with the strip 106 of elastic continues moving in the direction of arrow 102 out of surface groove 110 and off the drum 108. The flat web 100 with strip 106 of elastic passes through nip 114 to press and secure the strip 106 of elastic to the flat web 100. The nip 114 is defined by rolls 116 turning in the direction of arrows 118. In the alternative, any other suitable method for pressing and securing the strip 106 of elastic to the flat web 100 can be used. As the flat web 100 exits the nip 114, the flat web 100 can be drawn at a slower rate by the downstream process than the surface speed of rolls 116, allowing the strip 106 of elastic to contract and reduce the length of web 100.

Figure 6:
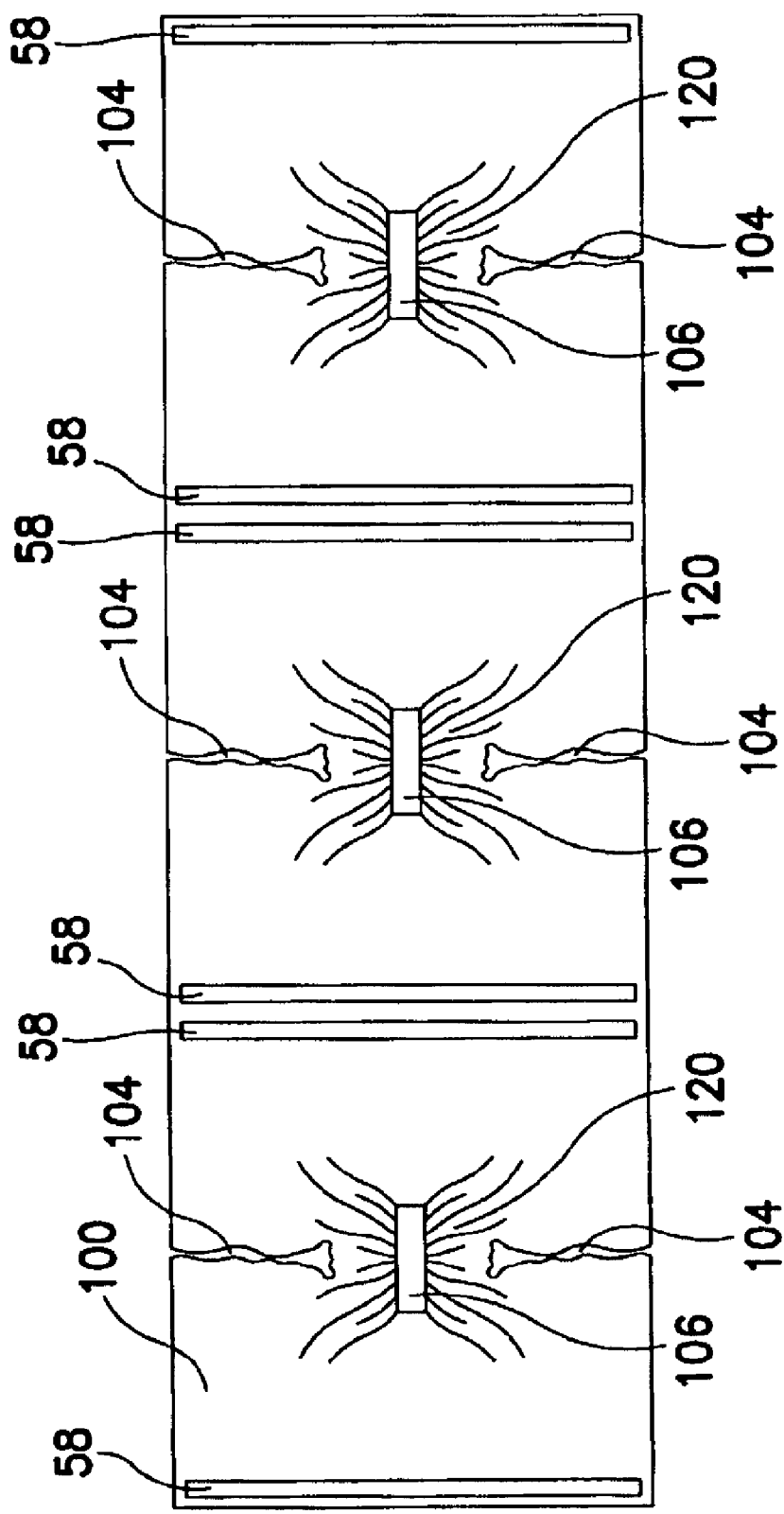
FIG. 6 is a top view of the flat web of FIG. 5 after contraction of the flat web.

FIG. 6 shows the flat web 100 after the contraction of the strips 106. The contraction of the flat web 100 defines contracted areas 120 in the selected areas between leg openings 104. The contracted area 120, as described more fully below, becomes the contracted crotch region 26 of the pant 10.

In the alternative, the strip 106 can be applied to the flat web 100 by any other method known in the art such as, for example, a corrugating drum such as that described in U.S. Pat. No. 4,397,704 issued Aug. 9, 1983 to Frick, an elastic application system in which the material is gathered into folds running in the cross-machine direction and a continuous elastic is applied in the machine direction and severed at the location of the folds in the base material such as described in U.S. Pat. No. 4,417,938 issued Nov. 29, 1983 to Sigl, an intermittent adhesive application that allows the elastic to snap back from non-adhesive zones, a high efficiency interface roll such as that described in U.S. Pat. No. 6,022,443 issued Feb. 8, 2000 to Rajala et al., U.S. Pat. No. 5,556,504 issued Sep. 17, 1996 to Rajala et al., and U.S. Pat. No. 6,319,347 issued Nov. 20, 2001 to Rajala et al., all of which are here incorporated by reference, or by any other any means known in the art.

Figure 11:
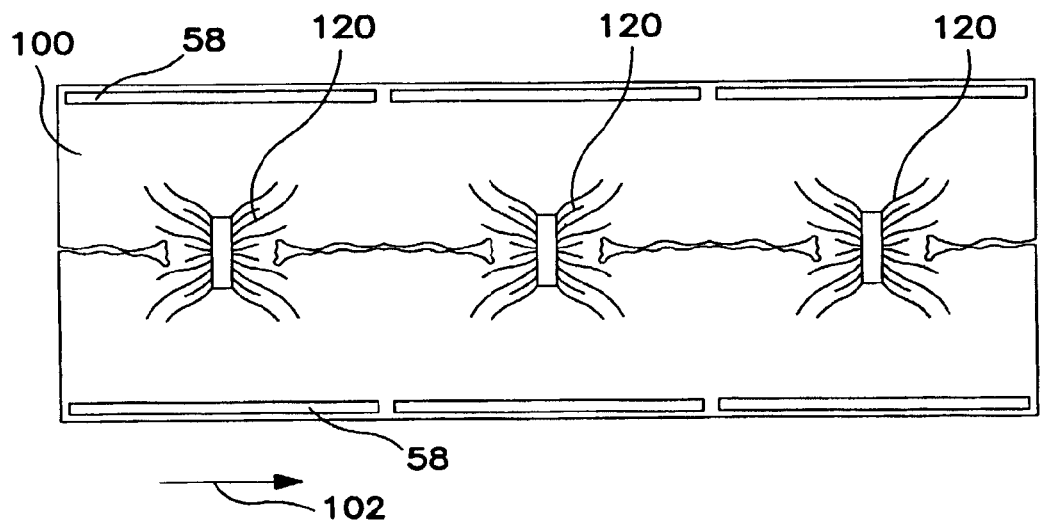
FIG. 11 is a top view of the flat web of FIG. 10 after contraction of the flat web.

FIGS. 6 and 11 also show waist elastics 58 applied to the flat web 100. The waist elastics 58 can be applied by any method known in the art at any stage in the manufacturing of the pant 10.

In the alternative, the tension on the flat web 100 can be reduced by cutting the flat web 100 into separate pieces approximately midway between successive strips 106 to define a garment shell 64 (FIG. 3C). It is also contemplated, however, that the step of cutting the flat web 100 can be carried out after contraction of the flat web 100.

Figure 8:
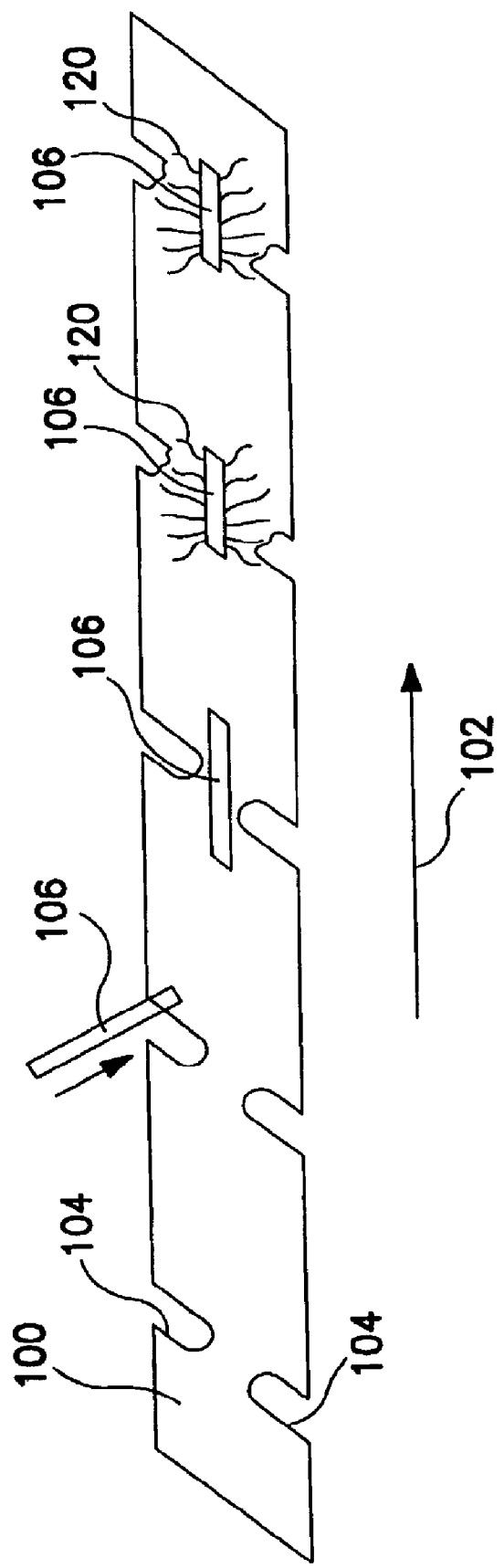
FIG. 8 is a side view of a process for applying a strip to the flat web.
Figure 9:
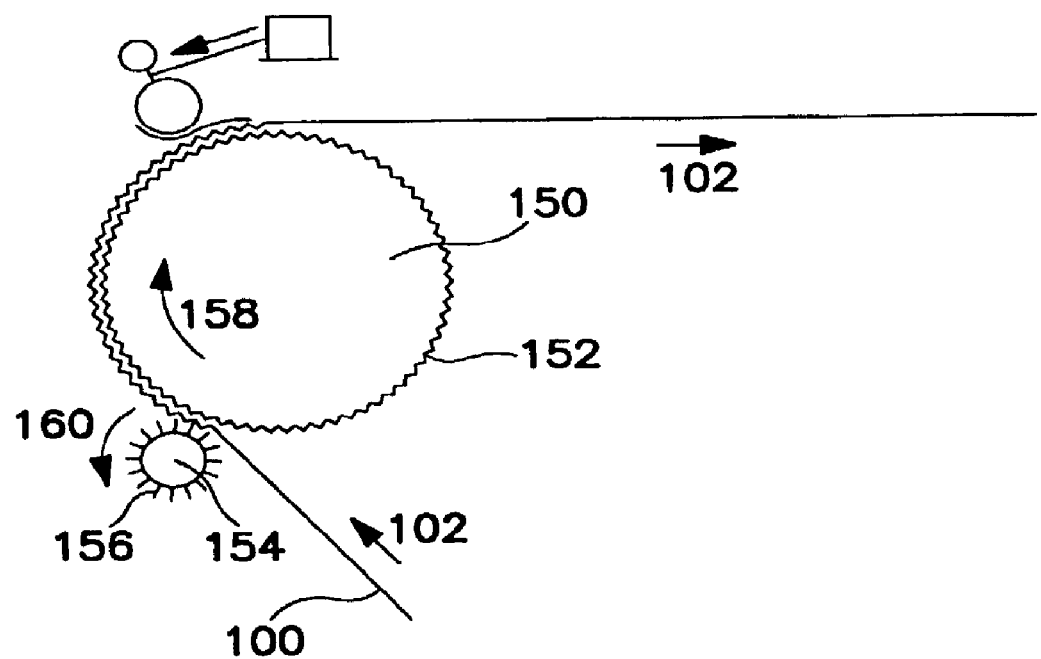
FIG. 9 is a side view of a corrugating drum for corrugating the flat web of FIG. 5.

Referring to FIG. 8, in the alternative, the strips 106, whether elastic or nonelastic, can be applied to the selected areas of the flat web 100 between the leg openings 104 by a cut and place module as is commonly known in the art.

Next, the flat web 100 can be contracted elastically or inelastically by any suitable means. For example, if the strip 106 is an elastic capable of delayed retraction, the flat web 100 can be contracted by activating the strip 106 to restore the elasticity by time, temperature, radiation or other appropriate energy. In the alternative, if the strip 106 is a heat shrinkable material, the flat web 100 can be contracted inelastically by activating the heat shrinkable material by applying heat or other appropriate energy.

In particular embodiments, the strips 106 are applied to the flat web 100 after contraction or pregathering of the flat web 100. In the machine direction, the flat web 100 can be pre-gathered by corrugating in the selected areas between the leg openings 104 by using a corrugating drum 150 (FIG. 9) in preparation for attachment of strip 106. Corrugating drums like corrugating drum 150 are known and are described, for example, in previously mentioned U.S. Pat. No. 4,397,704 issued Aug. 9, 1983 to Frick. Alternatively, a drum with discontinuous grooves that correlate with the location of strips 106 can be used. The flat web 100 travels around the drum 150 in the direction of arrow 158. Pressing roll 154 has teeth 156. The flat web 100 is pushed down into the grooves 152 by the teeth 156, thereby corrugating the flat web 100. Drum 150 and pressing roller 154 move in the direction of arrows 158 and 160, respectively.

Next, the strips 106 can be applied to the corrugated flat web 100 by a conventional cut and place applicator. Strips 106 can be attached to the web 100 using adhesive, thermal or ultrasonic bonding, or other means known in the art. Use of a corrugating drum or other device to pregather the flat web 100 permits the use of an unstretched elastic or of a non-elastic, non-retractive material such as a film or nonwoven material with properties similar to flat web 100. Alternatively, the strip

106 may include any of the previously described materials. The strips 106 maintain the corrugation in the contracted area 120 (FIG. 6).

Figure 12:
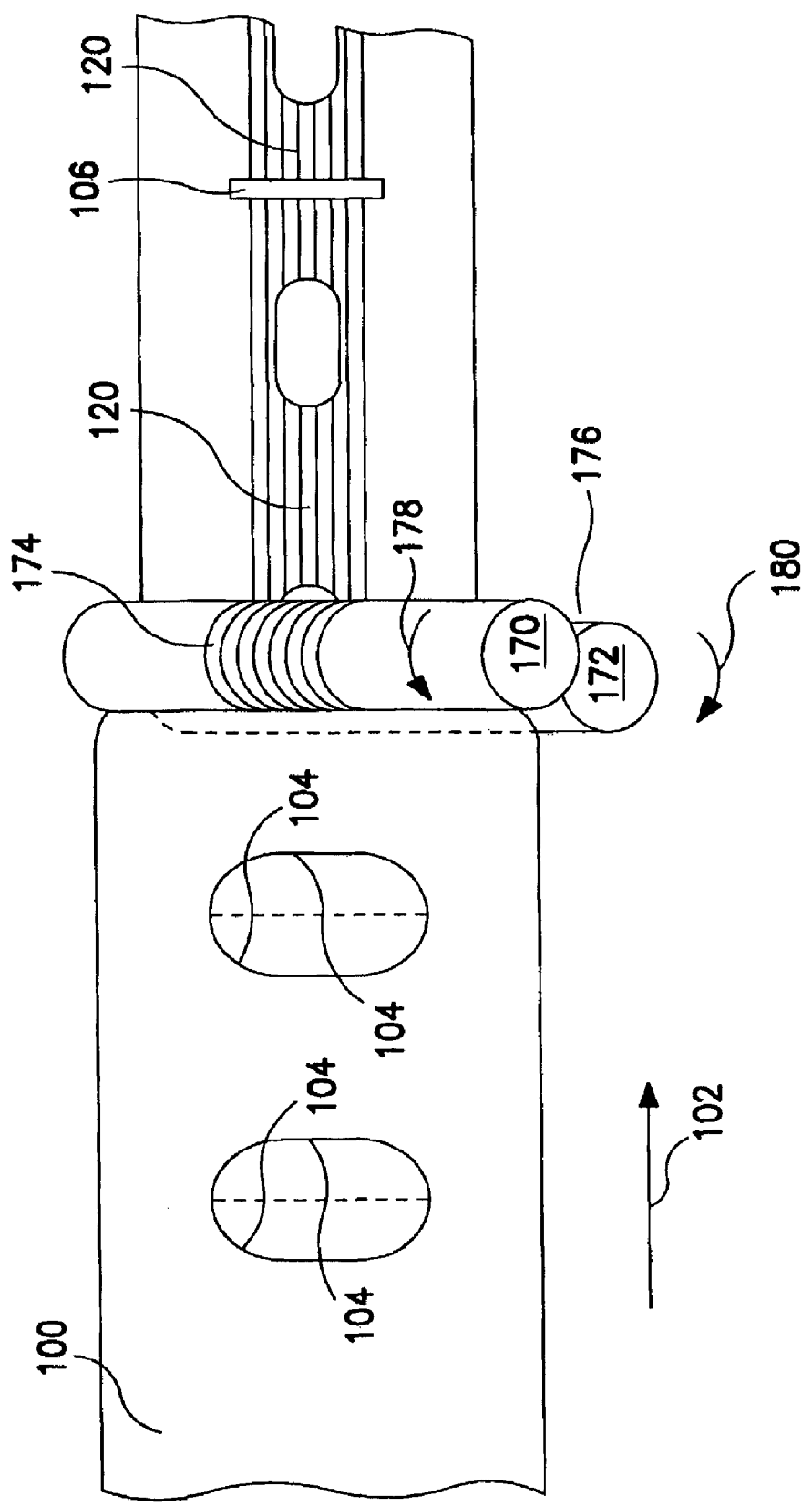
FIG. 12 is a side view of the flat web of FIG. 10 passing through corrugating rollers for corrugating the flat web of FIG. 10.

In the cross-machine direction process (FIGS. 10-12), portions of the flat web 100 are removed to define leg openings 104 by die cutting, or by any other suitable method known in the art. The leg openings 104, as more fully described below, become the leg openings 52 of the pant 10.

Figure 10:
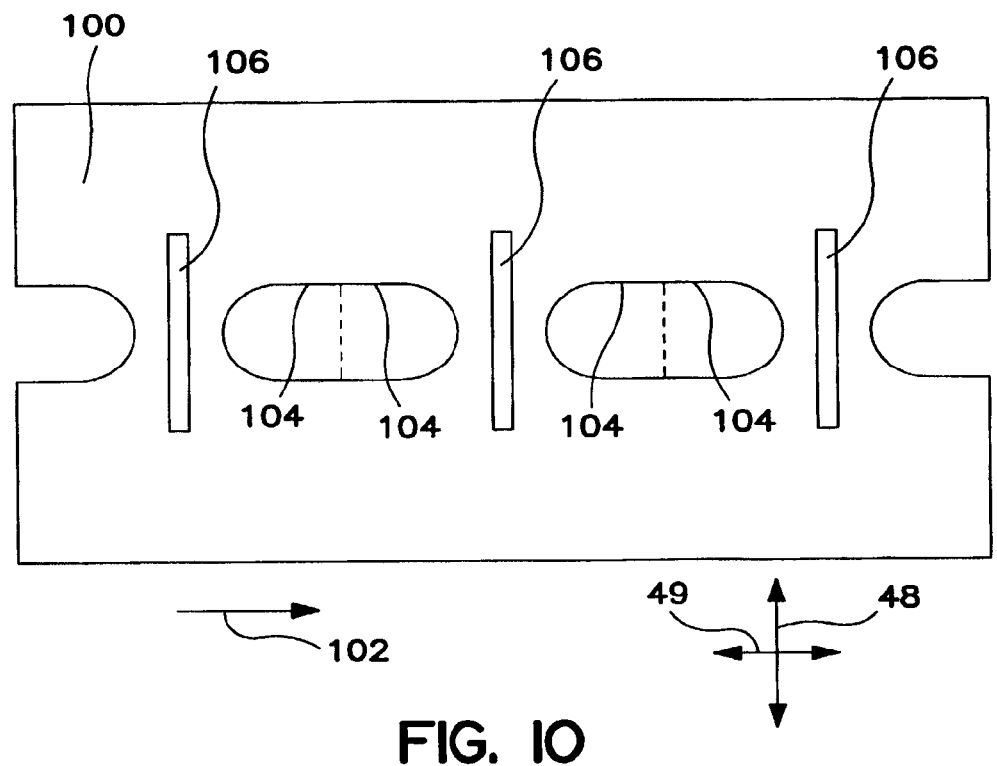
FIG. 10 is a top view of the flat web of FIG. 4 including leg openings and strips applied to the flat web for assembling pants according to one embodiment of the invention in the cross-machine direction.

As with the machine direction assembly process, strips 106 are applied to the selected areas located between the leg openings 104. In the cross-machine direction assembly process, strips are applied on the flat web 100 in an orientation perpendicular to arrow 102, as shown in FIG. 10.

The application of strip 106 of elastic material can be accomplished by a variety of methods, such as by moving the distal edges of the flat web 100 closer together and allowing the center portion of the web to become looped using the same principles of the previously described looper drum, but with the strip 106 being applied in an orientation perpendicular to arrow 102, or by other methods as are known in the art. As with the previously described looper drum, the flat web 100 can be fully extended again after application of the strip 106 in order to fully adhere the strip 106 to the web 100. In alternative embodiments, the strips 106 can be applied to the flat web 100 by a process in which an elastic or inelastic piece of material is cut, rotated and placed onto the flat web 100, for example, as described in U.S. Pat. No. 5,716,478 issued Feb. 10, 1998 to Boothe et al., U.S. Pat. No. 5,759,340 issued Jun. 2, 1998 to Boothe et al. and U.S. Pat. No. 4,608,115 issued Aug. 26, 1986 to Schroth et al., all of which are herein incorporated by reference, or by any other means known in the art. Where the strip 106 is a heat contractible material or a material capable of delayed retraction, the strip can be applied to web 100 as the web travels in the direction of arrow 102 (FIG. 10) in a flat and unlooped state.

Next the flat web 100 can be contracted elastically or inelastically by any of the previously described methods. FIG. 11 shows the flat web 100 after the contraction of the strips 100. The contraction of the flat web 100 defines contracted area 120 in the selected areas between the leg openings 104. The contracted area 120, as described more fully below, becomes the contracted crotch region 26 of the pant 10.

In particular embodiments, the strips 106 are applied to the flat web 100 after contraction or pregathering of the flat web 100. In the cross-machine direction, the flat web 100 can be pregathered by corrugating in the selected areas between the leg openings 104 by using intermeshing grooved rollers 170 and 172 (FIG. 12) in preparation for attachment of strip 106. Intermeshing grooved rollers like 170 and 172 are known in the art and are described, for example, in U.S. Pat. No. 5,755,902 issued May 26, 1998 to Reynolds, herein incorporated by reference. Roller 170 includes grooves 174 only in the middle portion of the roll to correspond to the desired location of the contracted area 120 on the flat web. The flat web 100 travels through nip 176 formed by rolls 170 and 172 in the direction of arrow 102. Roller 172 has complementary grooves (not shown) designed to intermesh with grooves 174 of roller 170. The flat web 100 is pushed into the grooves 174 by the complementary grooves on roll 172 to provide the corrugation in the contracted area 120. Rolls 170 and 172 move in the direction of arrows 178 and 180, respectively. The corrugations are held in place by attaching strips 106 on top of the corrugations.

The strip 106 can be applied to the corrugated flat web 100 by a cut and place module as is commonly known in the art and can be attached to the web using thermal, ultrasonic or adhesive bonding, or any other means known in the art. The strip 106 may include an inextensible material such as a film or nonwoven material with properties similar to web 100, or may include any of the previously described materials.

In either the machine direction process or the cross-machine direction process, the flat web 100 can now be cut into individual pieces, each of which will form a garment shell 64. The cutting can be accomplished by, for example, pinch cutting, shear cutting or any other means known in the art. As another alternative, the flat web 100 can be provided as separate pre-cut pieces each of which pre-cut separate pieces will eventually become a single garment shell 64, so that this cutting step could be skipped and the process could start with a pre-cut piece as the flat web 100. FIG. 3C shows the garment shell 64 prior to folding and formation of the side seams 54. As shown and as previously mentioned with respect to FIGS. 1, 2A, and 2B the garment shell 64 can include a front region 22, a back region 24, a contracted crotch region 26, an inner surface 28, and an outer surface 30 (not shown), front waist edge 38, back waist edge 39, and waist elastic member 58. The garment shell 64 can also include strip 106. It is also contemplated that the garment shell 64 can be made upside-down, i.e., with the inner surface 28 facing downwardly (not shown). The garment shell 64 can then be folded and the side seams 54 formed by any conventional method known in the art to form the pant 10 (without an absorbent structure). It is contemplated that the step of contracting the flat web 100 can occur either before or after the step of cutting into individual garment shells 64, and also before or after the formation of the side seams 54.

In either the machine direction process or the cross-machine direction process, in alternative embodiments, the strip 106 need not be a single strip of material. In particular embodiments, elastic strands or ribbons as are known in the art can be used instead of a single strip of material for strip 106. The elastic strands or ribbons can be straight or curved. In addition, in the embodiments in which the flat web is corrugated, it is contemplated that instead of attaching a strip 106, the corrugation in the contracted area 120 can be maintained by fusing or bonding the corrugations together in the selected areas between the leg openings 104. The corrugations can be bonded to themselves to hold them in place by adhesive, thermal or pressure bonding, or by any other means known in the art.

In the machine direction process, the strip 106 need not be a separate piece of material applied to the flat web 100. Instead, the flat web 100 may include an integral elastic zone aligned along the machine direction center line, instead of strip 106, with the elastic zone active in only the crotch region. Elastization of only the crotch region of the pant may be achieved by, for example, an elastic laminate structure in which the elastic is attached to the laminate using an intermittent adhesive. Intermittent adhesive application would allow the elastic to snap back from non-adhesive zones, which would be uncontracted as a result; contracted, adhesive-bearing zones can be located only in the crotch region of the garment. As an alternative, the elastic nature of certain regions may be inactivated by chopping or overbonding the elastic or other methods known in the art, for example, as described in U.S. Pat. No. 6,248,097 issued Jun. 19, 2001 to Beitz, herein incorporated by reference.

Referring to FIGS. 2A, 2B, 3A and 3B in particular embodiments, an absorbent structure 60 is included in the pant 10. The absorbent structure 60 can be introduced into the pant 10 in any suitable manner known in the art. In particular embodiments, the absorbent structure 60 can be placed on top of the contracted crotch region 26 on the inner surface 28 of the garment shell 64, either prior to formation of side seams 54 or after side seams 54 are made. It is also contemplated, however, that the absorbent structure 60 can be attached prior to contracting and/or cutting the flat web 100. Where the absorbent structure 60 is added to the pant 10 prior to formation of side seams 54, cut and place methods such as are known in the art may be used. Alternatively, for a closed pant (i.e., side seams already formed), the absorbent structure 60 may be inserted into the pant such as by the method described in the PCT Publication WO 02/52967 by Rabe, et al., or by other means as may be known in the art. The absorbent structure 60 can be attached to the garment shell 64 at the front waist edge 38 and back waist edge 39, or at some point below the front waist edge 38 and back waist edge 39 on the front region 22 and back region 24. Additionally or alternatively, the absorbent structure 60 can be attached in the contracted crotch region 26. The attachment can be accomplished by ultrasonic or adhesive bonding, or any other suitable method known in the art. As shown in FIGS. 2A and 2B, attachment to the front and back regions 22 and 24 provides for a loose fit in the contracted crotch region 26.

In particular embodiments, the absorbent structure 60 is stretchable or elasticizable in order to provide the desired close to the body fit for the absorbent structure 60 while the garment shell 64 hangs loosely. Alternatively, a suspension system for the absorbent structure may be required to provide a loose fit for the garment shell 64, such as described in U.S. Pat. No. 6,168,585 issued Jan. 2, 2001 to Cesco-Cancian, herein incorporated by reference.

The garment shell 64 with the absorbent structure 60 can then be folded and the side seams 54 formed by any conventional method known in the art to form the pant 10, as shown in FIGS. 2A and 2B. After folding the garment shell 64 and forming the side seams 54 (with or without an absorbent structure 60), if a temporarily inhibited elastic or latent elastic is used as the waist elastic 58, it may need to be activated to restore the elasticity.

The various components of the pant can be connected together by any means known to those skilled in the art such as, for example, adhesive, thermal and/or ultrasonic bonds, pressure bonds and also sewing and other methods used in durable garment manufacturing. Desirably, most of the components are connected using ultrasonic bonding for improved manufacturing efficiency and reduced raw material costs. For example, in particular embodiments, the side seams 54 are made using ultrasonic bonding. Certain garment manufacturing equipment which is readily known and understood in the art, including frames and mounting structures, ultrasonic and adhesive bonding devices, transport conveyors, transfer rolls, guide rolls, tension rolls, and the like, have not been shown in the Figures.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A pant including a garment shell made from a single flat web, the pant comprising:
   a garment shell, the garment shell including a front region, a back region, a contracted crotch region, side seams connecting the front region to the back region, two leg openings, and hanging legs, at least a portion of each of the front region, the back region, the contracted crotch region and the hanging legs comprising portions of the single flat web, wherein the hanging legs include no elasticization around a full periphery of the leg openings, the hanging legs being adapted to hang loosely about a wearer's thigh,
   wherein the side seams are positioned substantially midway between a central area of the front region and a central area of the rear region, on substantially opposed positions on the garment shell.

2. The pant of claim 1, further comprising a waist elastic extending along at least a portion of at least one of a front waist edge of the front region and a back waist edge of the back region.

3. The pant of claim 1, further comprising an absorbent structure attached to the garment shell in at least one of the front region, the back region and the crotch region.

4. The pant of claim 3, wherein the absorbent structure is attached to the garment shell by one of ultrasonic bonding and adhesive bonding.

5. The pant of claim 3, wherein the absorbent structure comprises a stretchable material.

6. The pant of claim 1, wherein a ratio of a take up to twice an inseam length is in a range from about 1:1 to about 1.5:1.

7. The pant of claim 1, wherein the single flat web consists essentially of a single, integral piece of material.

8. The pant of claim 1, wherein the web is corrugated in the contracted crotch region.

9. A pant including a garment shell made from a web, the pant comprising:
   a garment shell, the garment shell including a front region, a back region, a contracted crotch region, a front waist edge, a back waist edge, side seams connecting the front region to the back region, two leg openings, and hanging legs, at least a portion of each of the front region, the back region, the contracted crotch region and the hanging legs comprising portions of the web, the hanging legs being adapted to hang loosely about a wearer's thigh,
   wherein the side seams are positioned substantially midway between a central area of the front region and a central area of the rear region, on substantially opposed positions on the garment shell; and
   an absorbent structure attached to the garment shell in at least one of the front region, the back region, and the crotch region;
   wherein the contracted crotch region is positioned approximately midway between the side seams.

10. The pant of claim 9, further comprising a strip in the crotch region, the strip being positioned approximately midway between the side seams.

11. The pant of claim 10, wherein the contracted crotch region includes no intersecting elastomeric members.

12. The pant of claim 10, wherein the strip is straight.

13. The pant of claim 12, wherein the strip defines a length and extends in a direction substantially perpendicular to each waist edge along its entire length.

14. The pant of claim 9, wherein a ratio of a takeup of the garment shell on contraction of the crotch region to twice an inseam length is between about 1:1 and about 1.6:1.

15. The pant of claim 10, wherein the strip is elastomeric.

16. The pant of claim 9, wherein the garment shell is made from a flat web.

17. The pant of claim 9, wherein the web consists essentially of a single integral piece of material.

18. The pant of claim 9, wherein the web is corrugated in the contracted crotch region.

19. A pant including a garment shell made from a web, the pant comprising:
   a garment shell, the garment shell including a front region, a back region, a contracted crotch region, a front waist edge, a back waist edge, side seams connecting the front region to the back region, two leg openings and hanging legs, at least a portion of each of the front region, the back region, the contracted crotch region and the hanging legs comprising portions of the web,
   wherein the side seams are positioned substantially midway between a central area of the front region and a central area of the rear region, on substantially opposed positions on the garment shell;
   wherein the contracted crotch region is positioned approximately midway between the two leg openings, and the hanging legs include no elasticization around a full periphery of the leg openings, the hanging legs being adapted to hang loosely about a wearer's thigh.

20. The pant of claim 19, further comprising a strip in the contracted crotch region, the strip being positioned approximately midway between the two leg openings.

21. The pant of claim 20, wherein the contracted crotch region includes no intersecting elastomeric members.

22. The pant of claim 20, wherein the strip is straight.

23. The pant of claim 22, wherein the strip defines a length and extends in a direction substantially perpendicular to each waist edge along its entire length.

24. The pant of claim 19, wherein a ratio of a takeup of the garment shell on contraction of the crotch region to twice an inseam length is between about 1:1 and about 1.6:1.

25. The pant of claim 20, wherein the strip is elastomeric.

26. The pant of claim 19, wherein the garment shell is made from a flat web.

27. The pant of claim 19, further comprising an absorbent structure attached to the garment shell in at least one of the front region, the back region, and the crotch region.

28. The pant of claim 19, wherein the web is corrugated in the contracted crotch region.

29. A pant including a garment shell made from a web, the pant comprising:
   a garment shell, the garment shell including a front region, a back region, a contracted crotch region, a front waist edge, a back waist edge, two leg openings and hanging legs, a strip in the contracted crotch region positioned approximately midway between the two leg openings, at least a portion of each of the front region, the back region, the contracted crotch region and the hanging legs comprising portions of the web,
   wherein the side seams are positioned substantially midway between a central area of the front region and a central area of the rear region, on substantially opposed positions on the garment shell;
   wherein the strip is straight, defines a length, and extends in a direction substantially perpendicular to each waist edge along its entire length, and the hanging legs include no elasticization around a full periphery of the leg openings, the hanging legs being adapted to hang loosely about a wearer's thigh.

30. The pant of claim 29, wherein a ratio of a takeup of the garment shell on contraction of the crotch region to twice an inseam length is between about 1:1 and about 1.6:1.

31. A pant including a garment shell made from a web, the pant comprising:
   a garment shell, the garment shell including a front region, a back region, a contracted crotch region, a front waist edge, a back waist edge, side seams connecting the front region to the back region, two leg openings and hanging legs, and an absorbent structure attached to the garment shell in at least one of the front region, the back region, and the crotch region,
   wherein the side seams are positioned substantially midway between a central area of the front region and a central area of the rear region, on substantially opposed positions on the garment shell;
   at least a portion of each of the front region, the back region, the contracted crotch region and the hanging legs comprising portions of the web;
   the contracted crotch region being positioned approximately midway between the two leg openings, with an elastomeric strip positioned in the contracted crotch region approximately midway between the two leg openings;
   wherein the elastomeric strip is straight, defines a length, and extends in a direction substantially perpendicular to each waist edge along its entire length, and the hanging legs include no elasticization around a full periphery of the leg openings, the hanging legs being adapted to hang loosely about a wearer's thigh.

* * * * *